| United States Patent [19] | [11] Patent Number: 4,732,930 |
| Tanaka et al. | [45] Date of Patent: Mar. 22, 1988 |

[54] REVERSIBLE, DISCONTINUOUS VOLUME CHANGES OF IONIZED ISOPROPYLACRYLAMIDE CELLS

[75] Inventors: Toyoichi Tanaka, Newton; Yoshitsugu Hirokawa, Winchester, both of Mass.

[73] Assignee: Massachusetts Institute of Technology, Cambridge, Mass.

[21] Appl. No.: 735,910

[22] Filed: May 20, 1985

[51] Int. Cl.[4] .................. C08J 3/06; C08K 39/00; C08F 20/54
[52] U.S. Cl. .................................. 524/742; 524/555; 524/812; 524/744; 526/303.1; 526/306
[58] Field of Search ............................. 526/303.1, 306; 524/555, 812, 742, 744

[56] References Cited

U.S. PATENT DOCUMENTS

| 2,798,868 | 7/1957 | Miller | 526/303.1 |
| 3,075,956 | 1/1963 | Shields | 526/303.1 |
| 4,172,066 | 10/1979 | Zweigle | 526/306 |
| 4,358,355 | 11/1982 | Kalu | 526/306 |

Primary Examiner—Joseph L. Schofer
Assistant Examiner—Peter D. Mulcahy
Attorney, Agent, or Firm—Paul J. Cook

[57] ABSTRACT

An ionic gel formed by polymerization of isopropylacrylamide in the presence of an ion-containing monomer, a crosslinking agent and a suitable liquid medium is provided. The gel is capable of drastic volume change in response to solvent composition, temperature, pH, or ion composition.

4 Claims, No Drawings

REVERSIBLE, DISCONTINUOUS VOLUME CHANGES OF IONIZED ISOPROPYLACRYLAMIDE CELLS

BACKGROUND OF THE INVENTION

This invention relates to novel gel compositions which are capable of discontinuous volume change of several hundred times induced by infinitesimal changes in environment.

Gel is a form of material between the liquid and solid state. It consists of a crosslinked network of long polymer molecules with liquid molecules trapped within the network. Gels play important roles in various aspects of our everyday life.

In chemistry and biochemistry, gels are used extensively as matrices for chromatography and electrophoresesanalytical methods that separate molecules according to their molecular weights and charges. In these techniques, the pore size of the crosslinked polymer network plays an essential role in its sieving effects.

Gels also are important intermediate products in polymer products such as rubbers, plastics, glues and membranes.

In 1973, a new technique of light scattering spectroscopy was first introduced to gel studies. It was demonstrated that by measuring the intensity and the time dependence of fluctuations of laser light scattered from a gel, it is possible to determine the viscoelastic properties of the gel, that is, the elasticity of the polymer network and the viscous interaction between the network and the gel fluid. Recently, with the help of this powerful technique, very interesting phenomena in permanently crosslinked gels have been found: as the temperature is lowered, the polymer network becomes increasingly compressible, and at a certain temperature, it becomes infinitely compressible. At the same time, the effective pore size of the network increases and diverges. It is also observed that the volume of polyacrylamide gels ranges reversibly by a factor as large as several hundred by an infinitesimal change in external conditions such as solvent composition or temperature. Tanaka, Physical Review Letters, Vol. 40, No. 12, pp. 820-823, 1978 and Tanaka et al, Physical Review Letters, Vol. 38, No. 14, pp 771-774, 1977; Tanaka et al, Physical Review Letters 5, Vol. 45, pg 1636, 1980; Ilovsky, Macromolecules, Vol. 15, pg 782, 1982 and Hrouz et al, Europ. Polym. J., Vol. 17, pg 361, 1981.

It is known that copolymers of acrylamide and sodium acrylate in gel form are capable of drastic volume and it is also known that the gel showed continuous volume change when the concentration of the acrylic acid component, which was an ionizable group, was smaller than the critical value, while the change became discontinuous when the concentration of the acrylic acid component was greater than the critical value.

According to the conventional knowledge as described above, in order to prepare a polymer gel having the phase transition function with discontinuous volume change, it was believed necessary that the polymer contained a considerably large amount of the ionizable group.

The volume change of the conventional gels having an ionic group described above significantly depends on hydrogen ion concentration (pH) of the liquid medium to be used. Therefore, the conventional ionic gel could not be used when pH of the liquid medium could not be controlled sufficiently.

It is also known that polymers containing no ionizable group formed from a monomer containing a predominant amount of a N-substituted (metha)acrylamide and a crosslinking agent exhibit a drastic volume in water or mixtures of a solvent and water in response to change in liquid solvent composition. These gels do not depend upon hydrogen ion concentration of the liquid solvent. While these gels can be useful as a switching device or artifical muscle due to their ability to undergo discrete volume change cause by minute environmental changes, it would be desirable to provide gels which undergo greater volume changes in order to maximize the efficiency of the functions.

BRIEF DESCRIPTION OF THE FIGURES

FIG. 1 shows swelling curves of pure and ionized IPA gels with a wide range of ionic concentration.

FIG. 2 shows swelling curves of IPA gels with low ionic concentration showing a crossover from continuous to discontinuous phase transition.

FIG. 3 shows calculated and measured swelling curves of pure IPA gel. The curve (a) was calculated using $\Delta H_{est}$. The curve (b) represents the best fit result to the experimental data which are represented by triangles.

FIG. 4 shows calculated swelling curves of IPA gels are compared with experimental data. Numbers denote f values used in the calculation. Circles and triangles represent experimental data.

SUMMARY OF THE INVENTION

In accordance with this invention, it has been found that polymers containing ionized isopropylacrylamide exhibit the phase transition function with discontinuous volume change. The gel of this invention is composed of a polymerized product which is obtained by polymerization of isopropylacrylamide monomer, a source of metal ions, a crosslinking agent and a liquid medium selected from water, a solvent compatible with water and a mixture of said solvent and water. The polymeric product of this invention has such a reversible phase transition function that brings a drastic volume change in response to changes of the liquid medium composition temperature or ion concentration.

DESCRIPTION OF SPECIFIC EMBODIMENTS

The ionized gel of this invention has an advantage that it is usable in pure water, unlike presently available ionized gels.

The polymer which composes the non-ionic gel of this invention are obtained by polymerization of isopropylacrylamide monomer and a source of metal ions in the presence of a crosslinking agent. Suitable sources of metal ions include metal acrylates such as sodium acrylate, potassium acrylate, or lithium acrylate. These metal-containing monomers are incorporated into the gel by free radical polymerization mechanism. The minimum concentration of metal ions required to achieve drastic volume change is 10 mole percent based upon moles of isopropylacrylamide. To effect drastic volume change, the metal ion should be present between about 1 and 30 mole percent, preferably between about 3 and 15 mole percent based upon moles of isopropylacrylamide.

Representative crosslinking agents include N,N'-methylene-bis acrylamide, ethylene glycol dimethacrylate, glycerine triacrylate or divinylbenzene or the like. The concentration of crosslinkable monomer is generally about 0.3 to 3 mole percent based upon the isopropylacrylamide monomer which is the main component, but it is not particularly limited by these values. The crosslinking agent effects partial crosslinking of the polymerized isopropylacrylamide and provides a means to control the strength, swelling degree, phase transition temperature and the like of the non-ionic gel by changing the crosslinking density.

A mixture of these monomers can be polymerized using a polymerization initiator, e.g., a free radical initiator such as ammonium persulfate or sodium metal bisulfite, etc., with dilution with a solvent, e.g., water, a lower alcohol, hydrocarbon, etc., or without dilution. However, neither the solvent nor the polymerization initiator are always important factors to obtain the polymerized product from the monomer mixture, and any method suitable selected from the conventionally well-known gelation methods may be applied.

The crosslinked polymerized product thus obtained, which is insoluble in, and also not swelled in higher alcohol, is swelled in solvents such as water, dimethylsulfoxide, dimethylformamide, acetone, tetrahydrofuran, dioxane mixtures thereof and the like. Therefore, a purified polymerized product can be obtained by immersing the polymerized product in a suitable solvent to extract the unreacted monomers and other impurities.

As the liquid component of the gel of this invention, any of a solvent which has the affinity with the above-mentioned polymerized product and is compatible with water, for example, dimethylsulfoxide, dimethylformamide, acetone, tetrahydrofuran, alcohol and the like, water, or a mixture of said solvent and water can be employed.

The kind, combination and composition ratio of these liquid mediums have an influence on the critical conditions for the reversible phase transition of the gel of this invention, e.g., temperature, etc., and the composition of the liquid medium can also be a critical condition in itself. Accordingly, suitable selection of the kind and composition of the liquid mediums is required in accordance with the critical phase transition conditions desired for the gel. In any event, there exists a minimum critical concentration of metal ion for each solvent system employed in order to achieve reversible drastic volume change of the gel. This minimum metal ion concentration can be determined for each metal ion and solvent system by the procedure set forth in the Examples.

The guideline for selection of a solvent in which the phase transition occurs is to choose one which has the thetatemperature slightly lower than the desired phase transition temperature.

The ionic gel of this invention is prepared by swelling the above-said polymerized product in the liquid medium. The polymerized product having a low crosslinking degree absorbs a large amount of the liquid medium to form a gel having a large degree of swelling. The ionic gels of this invention thus prepared, however, never swell unlimitedly, but reach an equilibrium state in which the gel coexists with the excess liquid medium after swelling to its limit.

When the gel is in a swelled state, the liquid medium composition of the temperature of the gel can be changed to effect a drastic volume change of the gel. The non-ionic gel thus prepared is in a state wherein drastic phase transition when the composition of the liquid medium is changed to reach the critical composition, where the volume shrinks discontinuously by releasing the liquid medium. Alternatively, a reversal of the phase transition is effected at a different critical composition of the liquid medium where the gel volume swells discontinuously by absorbing the liquid medium. Furthermore, when temperature of the swelled gel is raised to exceed the critical temperature, the gel causes phase transition and releases the liquid medium, thereby shrinking the volume discontinuously. When the temperature drops below the critical temperature, the volume swells again discontinuously.

Using the following equation, it is possible to determine the critical temperature (Tc) of the phase transition:

$$Tc = \theta/(1 \pm 22.5 \, \phi_0)$$

where $\theta$ is the theta temperature of the network in the solvent, $\phi_0$ is the concentration of the polymer network at gelation. The sign in the denominator should be plus for gels which collapse at lower temperatures, and minus for gels which collpase at higher temperatures. The gel of this invention capable of drastic volume change can be used as an element to convert thermal energy to mechanical energy, a sensor element, a memory element and the like and, additionally, can be applied to various fields such as artificial organs, medical appliances, toys, as well as measuring instruments and switches.

The following examples illustrate the present invention and are not intended to limit the same.

EXAMPLE I

Ionic IPA gel was prepared by adding a predetermined amount of sodium acrylate ($CH_2CHCOONa$) to a pre-gel solution. The resulting gel contains COONa side chains. Then we wahed the gel with a large amount of water to replace all $Na^+$ by $H^+$. After washing, the gel has COOH side chains. The reason for replacing $Na^+$ by $H^+$ is as follows. Physical properties of a gel containing COONa group must depend on an amount of solvent used in the experiment because the dissociation of COONa changes with the concentration of $Na^+$ in the solvent. On the other hand, ionic gel containing only COOH group should give reproducible results irrespective of an amount of solvent when pure water is used as a solvent.

Compositions of gels we prepared are tabulated in Table 1. The concentration of N,N'-methylene bisacrylamide is constant for all the gels (8.6 mM). The amounts of ammonium persulfate or sodium meta bisulfite initiators are 20 mg each for 100 ml of solution. It should be noted that in each of these gels, the total concentration of the network constituents (IPA+sodium acrylate+bisacrylamide) is the same (708.6 mM).

In an actual procedure of preparation, a gelation reaction was made to occur in micropipets with an internal diameter of 1.3 mm. After gel is formed, it was removed from the micropipets and soaked in large amounts of water, e.g., 1 liter, to wash out $Na^+$ ions and unreacted reagents. Water was refreshed every day. As the replacement of $Na^+$ by $H^+$ proceeds, gel volume decreases because the dissociation constant of COOH is smaller than that of COONa. The diameter of the gel was measured every day. After about half a month, gel diameter reached a constant value and no longer changed with time, which showed that essentially all Na+ ions were replaced by H+.

Swelling curve measurement was made by measuring a diameter of a gel as a function of temperature with a low-power microscope equipped with a calibrated reticle. A temperature controlled water bath was used to keep temperature of a gel constant for a long period. The stability of temperature was better than ± 0.04° C. per day. Near the transition point the sample temperature was kept constant for at least 36 hours before the measurement was made. Even far from the transition point, the gel was kept at a constant temperature for 24 hours to assure the true equilibrium state to be attained.

Swelling curves measured on a series of gels are shown in FIG. 1. It is seen that pure IPA gel (#1) undergoes a continuous volume change around 34.3° C., whereas gels with high ionic concentration show discontinuous transitions. The transition temperature goes higher as the ionic concentration increases, and for the gel with the highest ionic concentration (128 mM), no transition was observed up to 80° C. It should be noted that in the shrunken side, all the swelling curves merge into a single curve. This is consistent with the fact that the total concentration of network constituents are set equal in all the gels.

FIG. 2 shows the crossover from a continuous to a discontinuous transition more precisely. It is seen that the gels #1 to #3 undergo a continuous transition, whereas the gel #4 shows a discontinuous transition. Thus, the critical composition lies between those of #3 and #4 (ionic concentration between 2 and 4 mM), and that the critical temperature is about 34.6° C.

The above conclusion as to the order of transition was further supported by visual observation of gels under miroscope during the transition. Namely, in the temperature range corresponding to the largest volume change gels #4 to #9 deformed irregularly, and at higher temperatures the gel became homogeneous again. In contrast, gels #1 to #3 showed a smooth volume change without irregular deformation. The irregular deformation must result from coexistence of two phases with unequal densities, and thus provides direct evidence that the transition is first order.

A phase transition of a gel has been discussed on the basis of a mean field theory of gel swelling. According to this theory, the Gibbs free energy of a gel can be expressed as follows:

$$\Delta G = G - G_0 = kT \{n\ln(1 - \phi) + \chi n\phi\} + 3\frac{kT}{2} v_0(\alpha^2 - 1 - \ln\alpha) - v_0 fkT \ln\left(NV_0 \frac{\alpha^3}{V_1}\right). \quad (1)$$

Here, $G_0$ is the sum of free energies of pure solvent and an ordered collection of polymers, n the number of solvent molecules in a gel, $\phi$ the volume fraction of polymers, $\chi$ the polymersolvent interaction parameter, $v_0$ the total number of chains in a gel, $\alpha$ the linear expansion coefficient, $V_0$ the volume of a gel when its network has a random walk configuration, $V_1$ the molar volume of solvent, k the Boltzmann constant, T the absolute temperature, N the Avogadro's number and f the number of counter ions per chain. The first term on the right-hand side of Eq. (1) represents "mixing free energy", the second term represents the rubber elasticity, and the third is the ion pressure term. For a nonionic gel the last term is absent.

The equilibrium volume fraction of polymers can be obtained from this free energy by imposing the equilibrium condition, which in the present case, is the condition of zero osmotic pressure. This can be written as $$\pi = -\frac{N}{V_1}\left(\frac{\partial \Delta G}{\partial n_1}\right)_{T,P} = 0. \quad (2)$$

From Eqs. (1) and (2) the osmotic pressure of a gel is obtained as follows:

$$\pi = \pi_{mix} + \pi_{elas} + \pi_{ion} \quad (3)$$

$$= -\frac{NkT}{V_1}\{\phi + \ln(1 - \phi) + \chi\phi^2\} + vkT\left\{\frac{1}{2}\left(\frac{\phi}{\phi_0}\right) - \left(\frac{\phi}{\phi_0}\right)^{\frac{1}{3}}\right\} + vfkT\left(\frac{\phi}{\phi_0}\right).$$

Here $\phi_0$ is the volume fraction of polymers when the gel network has a random walk configuration and $v$ is the number of chains in a unit volume of a gel at $\phi = \phi_0$.

To calculate the temperature dependent swelling ratio, temperature dependence of X is taken explicitly in to account. Thus, $$X = \frac{\Delta F}{2kT} \quad (4)$$

$$= \frac{(\Delta H - T\Delta S)}{2kT},$$

where $\Delta F$ represents the difference in the free energy of a solvent molecule that is immersed in pure polymer compared with one that is surrounded entirely by molecules of the same kind, $\Delta H$ and $\Delta S$ are the corresponding enthalpy and entropy changes, respectively. Using Eqs. (2), (3) and (4), an equation relating the equilibrium concentration of a gel to temperature is as follows:

$$\frac{1}{T} = \frac{\Delta S}{\Delta H} + \frac{k}{\Delta H}\left[V_1\frac{v}{N\phi^2}\left\{(2f + 1)\left(\frac{\phi}{\phi_0}\right) - 2\left(\frac{\phi}{\phi_0}\right)^{\frac{1}{3}}\right\} - \frac{2}{\phi} - \frac{2\ln(1 - \phi)}{\phi^2}\right]. \quad (5)$$

Among the parameters in Eq. (5), $\phi_0$ can be estimated fairly accurately from the experimental asymptotic value of $V/V_0$ toward high temperature, i.e., $\phi_0 \approx 0.065 \sim 0.075$. Also, the maximum number of $v$ can be estimated from an amount of crosslinker used, i.e., $v_{max} \approx 1.0 \times 10^{22} 1^{-1}$. $\Delta H$ of IPA molecule can be estimated from the solubility parameter. The value of $\Delta H$ so estimated is $\Delta H_{est} \approx -1.6 \times 10^{-12}$ erg. It is clear from Eq. (5) that the transition temperature is mainly determined by the ratio $\Delta S/\Delta H$, while the curvature of a swelling curve is mainly determined by $\Delta H$.

In FIG. 3 the swelling curve of non-ionic gel calculated using $\Delta H_{est}$ is compared with the measured curve. The value of $\Delta S$ was determined such that the transition temperature coincides with the measured value, i.e., $\Delta S = -5.4 \times 10^{-15} erg \cdot K^{-1}$. Other parameter values used were $\phi_0 = 0.07$, $\nu = 1.0 \times 10^{22} 1^{-1}$. It is seen that the fit is poor in a quantitative sense. The calculated curve shows much milder changes than the measured curve in the transition region.

It turned out that a better quantitative fit can only be obtained by ignoring the estimations of $\Delta H$ and $\nu$ mentioned above. The best fit result is also shown in FIG. 3. The parameters used were $\Delta H = -5.4 \times 10^{-11} erg$, $\Delta S = -1.8 \times 10^{-13} erg \cdot K^{-1}$, $\nu = 1.2 \times 10^{24} 1^{-1}$ and $\phi_0 = 0.07$. Using these parameters, swelling curves for ionic gels are also calculated. The result is shown in FIG. 4 together with the experimental data. The first order transition temperatures were determined by calculating the free energy using Eq. (1). Namely, the temperature at which depths of double minima in the free energy curve become equal with each other was taken to be a transition temperature. The calculated curves fit the experimental data fairly well. Thus, Eq. (5) can explain the experimental result at least semi-quantitatively.

The results are semi-quantitative for the following reasons. First, the values of $\Delta H$ and $\nu$ are both much larger than the estimated ones and thus can not easily be acceptable. The model underlying Eq. (1) is too simple to simulate a structure of real gel. Discrepancies from an ideal network, e.g. side chains and entanglement, should play an important role in a real gel, though such effects are not taken into account in Eq. (1). The parameter values may be regarded as the "effective values" which incorporates the inadequacy of the model.

Second, the values of f which fit the measured swelling curve are not consistent with the concentration of ionic groups $X_f$ and $\nu$. As seen in FIG. 4, the swelling curves of gels #5 (8 mM) and #6 (32 mM) fit well with the calculated curves with f=1 and 2, respectively. In these gels, however, even if the dissociation is complete, f cannot be larger than $4 \times 10^{-3}$ and $1.6 \times 10^{-2}$, respectively, if $\nu$ is put equal to $1.2 \times 10^{24} 1^{-1}$. Thus, there arises a question whether the effect of ions is adequately described by the third term of Eq. (1) (or equivalently by the third term of Eq. (3)).

TABLE 1

Composition of IPA Gels.
Concentration of Monomers are Given in mM.
IPA: Isopropylacrylamide, SA: Sodium-acrylate.

| | 1 | 2 | 3 | 4 | 5 | 6 | 7 | 8 | 9 |
|---|---|---|---|---|---|---|---|---|---|
| IPA | 700 | 699 | 698 | 696 | 692 | 668 | 650 | 630 | 572 |
| SA | 0 | 1 | 2 | 4 | 8 | 32 | 50 | 70 | 128 |

We claim:

1. An ionic gel having a reversible phase transition function characterized by a drastic volume change in response to a change of liquid medium composition, temperature, pH or ion composition which comprises a polymerized product obtained by polymerization of isopropylacrylamide in the presence of an ion-containing monomer selected from the group consisting of a metal-containing acrylate and a metal containing methacrylate, a crosslink agent and a liquid medium selected from the groups consisting of water, a solvent compatible with water and a mixture of said solvent and water, said ion containing monomer being ion exchanged to replace said metal with hydrogen ion subsequent to said polymerization.

2. A non-ionic gel according to claim 1, in which said solvent compatible with water is a solvent selected from the group consisting of acetone, dioxane and dimethyl sulfoxide.

3. An ionic gel having a reversible phase transition function characterized by drastic volume change in response to a change of liquid medium composition, pH or ion composition or temperature which comprises a polymerized product obtained by polymerization of isopropylacrylamide and an ion-containing monomer selected from the group consisting of a metal containing acrylate and a metal containing methacrylate in the presence of N,-methylene-bisacrylamide and a liquid medium selected from the group consisting of water, a solvent compatible with water and a mixture of said solvent and water, said ion container monomer being ion exchanged to replace said metal with hydrogen ion subsequent to said polymerization.

4. A non-ionic gel according to claim 3, in which said solvent compatible with water is a solvent selected from the group consisting of acetone, dioxane and dimethyl sulfoxide.

* * * * *